(12) United States Patent
Crampton et al.

(10) Patent No.: US 8,980,780 B2
(45) Date of Patent: Mar. 17, 2015

(54) REGENERATING A TITANIUM SILICALITE CATALYST

(75) Inventors: Hannah L. Crampton, Lake Jackson, TX (US); Philip J. Carlberg, Lake Jackson, TX (US); Cesar E. Meza, Pearland, TX (US)

(73) Assignee: Dow Global Technologies LLC, Midland, MI (US)

( * ) Notice: Subject to any disclaimer, the term of this patent is extended or adjusted under 35 U.S.C. 154(b) by 4 days.

(21) Appl. No.: 13/983,345

(22) PCT Filed: Feb. 3, 2012

(86) PCT No.: PCT/US2012/023823
§ 371 (c)(1),
(2), (4) Date: Aug. 2, 2013

(87) PCT Pub. No.: WO2012/106627
PCT Pub. Date: Aug. 9, 2012

(65) Prior Publication Data
US 2013/0309152 A1 Nov. 21, 2013

Related U.S. Application Data

(60) Provisional application No. 61/439,687, filed on Feb. 4, 2011.

(51) Int. Cl.
| | | |
|---|---|---|
| *B01J 38/48* | (2006.01) | |
| *B01J 21/20* | (2006.01) | |
| *B01J 29/89* | (2006.01) | |
| *B01J 29/90* | (2006.01) | |
| *B01J 38/52* | (2006.01) | |
| *B01J 38/70* | (2006.01) | |
| *C07D 301/12* | (2006.01) | |
| *B01J 21/06* | (2006.01) | |

(52) U.S. Cl.
CPC *B01J 21/20* (2013.01); *B01J 29/89* (2013.01); *B01J 29/90* (2013.01); *B01J 38/52* (2013.01); *B01J 38/70* (2013.01); *C07D 301/12* (2013.01); *B01J 21/063* (2013.01); *Y10S 502/514* (2013.01)
USPC .......................................... 502/22; 502/514

(58) Field of Classification Search
USPC ................ 502/22, 27, 28, 29, 33, 31, 514
See application file for complete search history.

(56) References Cited

U.S. PATENT DOCUMENTS

| | | |
|---|---|---|
| 4,117,066 A | 9/1978 | Mollet et al. |
| 4,370,240 A | 1/1983 | Brownell et al. |
| 5,252,758 A | 10/1993 | Clerici et al. |
| 5,620,935 A | 4/1997 | Thiele |
| 5,952,530 A | 9/1999 | Argyropoulos |
| 6,063,941 A | 5/2000 | Gilbeau |
| 6,169,050 B1 | 1/2001 | Catinat et al. |
| 6,288,248 B1 | 9/2001 | Strebelle et al. |
| 6,818,132 B2 | 11/2004 | Haubs et al. |
| 7,323,578 B2 | 1/2008 | Catinat et al. |
| 7,705,167 B2 | 4/2010 | Shinorhara et al. |
| 7,838,455 B2 | 11/2010 | Kwak et al. |
| 8,534,963 B2 | 9/2013 | Luik |
| 2006/0016760 A1 | 1/2006 | Bozak et al. |
| 2009/0018291 A1 | 1/2009 | Kwak et al. |
| 2010/0264091 A1 | 10/2010 | Nazzer |
| 2011/0137054 A1 | 6/2011 | Postma et al. |
| 2012/0130095 A1 | 5/2012 | Crampton et al. |

FOREIGN PATENT DOCUMENTS

| | | |
|---|---|---|
| CN | 101237928 | 8/2008 |
| CN | 101747296 | 6/2010 |
| CN | 101747297 | 6/2010 |
| CN | 101279958 | 10/2010 |
| DE | 19962719 | 6/2001 |
| WO | 2008087657 | 7/2008 |
| WO | 2009063487 | 5/2009 |

OTHER PUBLICATIONS

Thiele, G.F. and Roland, E., "Propylene epoxidation with hydrogen peroxide and titanium silicalite catalyst: Activity, deactiviation, and regeneration of the catalyst," Journal of Moelcular Catalysis A: Chemical 117 (1997) 351-356.
Clerici, Mario G.; Ingallina, Patrizia. "Epoxidation of lower olefins with hydrogen peroxide and titanium silicalite." Journal of Catalysis, 1993, 140, 71-83.
Zhang, Zhaoguang; Kang, Jingna, Yaquan. "Effects of organic solvent addition on the epoxidation of propene catalyzed by TS-1." Reaction of Kinetics and Catalysis Letters 2007, 92(1), 49-52.
Gea Westfalia Separatpr; "Separation, Solution, Success"; 2010.

*Primary Examiner* — Edward Johnson
(74) *Attorney, Agent, or Firm* — Brooks, Cameron & Huebsch, PLLC

(57) ABSTRACT

A process for regenerating a titanium silicalite catalyst by contacting the fouled titanium silicalite catalyst with a regeneration solution that includes at least one oxidizing agent.

19 Claims, 2 Drawing Sheets

REGENERATING A TITANIUM SILICALITE CATALYST

CROSS-REFERENCE TO RELATED APPLICATIONS

This application is a National Stage application under 35 U.S.C. 371 of PCT/US2012/023823, filed on Feb. 3, 2012 and published as WO 2012/106627 on Aug. 9, 2012, which claims the benefit of U.S. Provisional Application Ser. No. 61/439,687 filed Feb. 4, 2011, the entire contents of which are incorporated herein by reference in its entirety.

FIELD OF DISCLOSURE

Embodiments of the present disclosure are directed to catalysts, and more particularly to a process for regenerating a titanium silicalite catalyst.

BACKGROUND

Titanium silicalite catalysts can be used in epoxidation reactions to form oxiranes. Oxiranes are compounds that are useful in a variety of end use applications. Epichlorohydrin ("epi"), for example, is an oxirane that can be used to make epoxy resins. The epoxidation reaction can include reacting an olefin with a peroxide compound in the presence of a catalyst and a solvent mixture with an alcohol and one or more non-reactive co-solvent(s). For example, allyl chloride can react with hydrogen peroxide to form epichlorohydrin.

Titanium silicalite catalysts can become fouled during the epoxidation reaction. For example, titanium silicalite catalysts have small pores that can become plugged over time by organic materials in the epoxidation reaction. Using a fouled titanium silicalite catalyst in the epoxidation reaction can reduce the amount of oxirane produced, thereby increasing the cost of production.

SUMMARY

One or more embodiments of the present disclosure include a process for regenerating a titanium silicalite catalyst fouled during a reaction between an olefin and a peroxide compound to produce an oxirane. The process includes contacting the fouled titanium silicalite catalyst with a regeneration solution that includes at least one oxidizing agent to provide a regenerated titanium silicalite catalyst. In one or more embodiments, this process employs a regeneration solution that has an oxidizing agent concentration of less than 0.50 weight percent (wt %) based on a total weight of the regeneration solution, exclusive of the titanium silicalite catalyst.

One or more embodiments of the present disclosure include a regenerated titanium silicalite catalyst obtainable by a process as provided herein. In addition, one or more embodiments of the present disclosure include a process for regenerating a titanium silicalite catalyst fouled during a reaction between an olefin and a peroxide compound to produce an oxirane. The process includes contacting the fouled titanium silicalite catalyst with a regeneration solution including at least one oxidizing agent to provide a regenerated titanium silicalite catalyst, wherein the regeneration solution has a pH of less than 2.

Certain embodiments of the process of the present disclosure include a "washing step," for example, a pre-regeneration washing step, wherein a fouled titanium silicalite catalyst is contacted with a washing solution prior to contact with the regeneration solution, and/or a post-regeneration washing step, wherein a regenerated titanium silicalite catalyst is contacted with a washing solution following contact with the regeneration solution. The washing solution comprises a suitable organic compound, for example, but not limited to, aliphatic, cyclic, aromatic, halogenated, supercritical, or alcoholic organic diluents. For example, the washing solution comprises the organic compound(s) methanol and/or water. In one embodiment, the washing solution comprises methanol. For one or more embodiments, the washing step is carried out for a time period within a range of from 5 minutes to 60 minutes, preferably for 30 minutes.

Alternative embodiments of the present disclosure include a process for regenerating a titanium silicalite catalyst fouled during a reaction between an olefin and a peroxide compound to produce an oxirane, wherein the washing step is eliminated by contacting the titanium silicalite catalyst to be regenerated with a regeneration solution that comprises at least one oxidizing agent and further comprises an organic compound. Thus, in certain embodiments of the disclosure, a fouled titanium silicalite catalyst is not subjected to a pre-regeneration wash and/or post-regeneration wash.

The present disclosure provides therefore a process for regenerating a titanium silicalite catalyst fouled during a reaction between an olefin and a peroxide compound to produce an oxirane, the process comprising contacting the fouled titanium silicalite catalyst with a regeneration solution including at least one oxidizing agent to provide a regenerated titanium silicalite catalyst, wherein the regeneration solution has an oxidizing agent concentration of less than 0.50 weight percent based on a total weight of the regeneration solution prior to contact with the fouled titanium silicalite catalyst, exclusive of the titanium silicalite catalyst. Also provided is a process for regenerating a titanium silicalite catalyst fouled during a reaction between an olefin and a peroxide compound to produce an oxirane, the process comprising contacting the fouled titanium silicalite catalyst with a regeneration solution including at least one oxidizing agent to provide a regenerated titanium silicalite catalyst, wherein the regeneration solution has a pH of less than 2. Additionally, the present disclosure provides a process for regenerating a titanium silicalite catalyst fouled during a reaction between an olefin and a peroxide compound to produce an oxirane, the process comprising the step of contacting the fouled titanium silicalite catalyst with a regeneration solution comprising at least one oxidizing agent and further comprising an organic compound to provide the regenerated titanium silicalite catalyst, with the proviso that the process does not comprise a washing step in addition to the contacting step. In addition, the present disclosure provides a regenerated titanium silicalite catalyst obtainable by any one of the above-referenced processes.

The above summary of the present disclosure is not intended to describe each disclosed embodiment or every implementation of the present disclosure. The description that follows more particularly exemplifies illustrative embodiments. In several places throughout the application, guidance is provided through lists of examples, which examples can be used in various combinations. In each instance, the recited list serves only as a representative group and should not be interpreted as an exclusive list.

DETAILED DESCRIPTION

Figure 1:
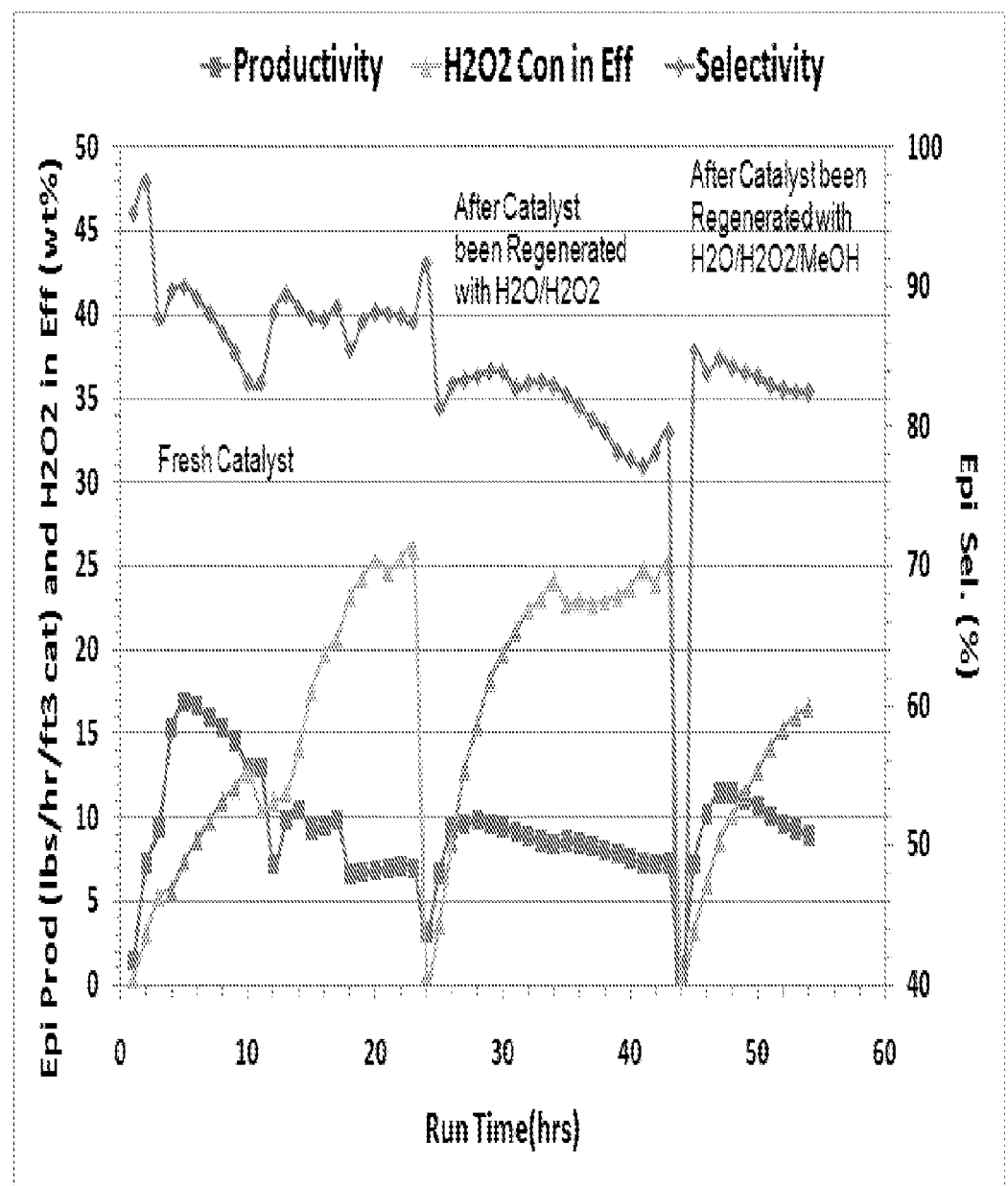
FIG. 1 is a graph depicting epi productivity, epi selectivity and $H_2O_2$ concentration data generated by a process according to certain embodiments of the present disclosure.

Embodiments of the present disclosure are directed to a process for regenerating a titanium silicalite catalyst that has been fouled during a reaction between an olefin and a peroxide compound to produce an oxirane, where such a reaction may also be referred to as an "epoxidation reaction." For one or more embodiments, the titanium silicalite catalyst can be regenerated by contacting the fouled titanium silicalite catalyst with a regeneration solution including an oxidizing agent.

The amount of oxirane produced by the titanium silicalite catalyst is referred to as the "activity" of the catalyst. As discussed herein, the titanium silicalite catalysts (also referred to herein as "catalyst") can become fouled as the small pores of the titanium silicalite catalyst become plugged during the epoxidation reaction. When a titanium silicalite catalyst becomes fouled, the yield of the oxirane (e.g., epichlorohydrin, also referred to herein as "epi") during the epoxidation reaction can decrease. Thus, the phrase "fouled catalyst" refers to the performance of the catalyst. As mentioned above, a "fouled catalyst" is a catalyst that is contaminated with foulants, e.g., plugged with organic materials from the epoxidation reaction. As a result, access of the reactants to the catalyst is reduced and/or the catalytic activity of a fouled catalyst is reduced as compared to that of a corresponding fresh catalyst. For example, a fouled catalyst has decreased selectivity and/or decreased productivity and/or decreased yield as compared to a corresponding fresh catalyst. Thus, under the same operating conditions, the use of a fouled catalyst results in a decreased oxirane yield as compared to that of a corresponding fresh catalyst, e.g., at least about a 25% decrease in epi productivity, and/or at least a 4% decrease in epi yield.

Once fouled, the titanium silicalite catalyst can be regenerated according to the methods of the present disclosure. Thus, a "regenerated catalyst" is a catalyst having a portion of its original catalytic activity renewed and/or restored.

As used herein, "oxirane yield" and/or "epichlorohydrin yield" is represented as a percentage and is determined by dividing the amount of oxirane produced during the epoxidation reaction by a theoretical maximum amount of oxirane produced at 100 percent (%) of the peroxide compound conversion to the oxirane.

As used herein, the phrase "epichlorohydrin productivity" refers to the amount of epi produced (i.e., the mass rate (per unit time)) divided by the catalyst amount (in volume). Epi productivity is expressed in lbs of Epi/hr/ft$^3$ of catalyst.

As used herein, the phrase "epichlorohydrin selectivity" refers to the ratio of the molar amount of epi produced divided by the sum of the molar amount of epi produced and molar amount of byproduct produced, such as 1-chloro-2,3-dihydroxypropane ("MCH") and 1-chloro-3-methoxy-2-hydroxypropane ("CMP"), and is expressed as a percentage.

Previous approaches have regenerated fouled titanium silicalite catalysts by using thermal oxidation techniques. Thermal oxidation techniques can include a heat treatment by flowing gas through the fouled catalyst or static calcination. However, thermal oxidation techniques are not practical methods for in situ regeneration of a catalyst in a reactor due to the materials of construction that are used for the required temperatures of thermal oxidation, approximately 600 degrees Celsius (° C.). Additionally, other approaches have used chemical oxidation as an alternative to using thermal oxidation. However, these approaches use an oxidizing agent not present in the epoxidation reaction. Using an oxidizing agent not present in the epoxidation reaction can cause contamination and increase the cost of production by adding additional materials used during the epoxidation reaction.

As used herein, "a," "an,", "the," "at least one," and "one or more" are used interchangeably.

The terms "includes" and "comprises" and variations thereof do not have a limiting meaning where these terms appear in the description and claims. Thus, for example, a solvent mixture with an alcohol and a non-reactive co-solvent can be interpreted to mean that the solvent mixture includes one or more alcohol(s) and one or more non-reactive co-solvent(s).

The words "preferred" and "preferably" refer to embodiments of the invention that may afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments form the scope of the invention.

Also herein, the recitations of numerical ranges by endpoints include all numbers subsumed within that range (e.g., 1 to 5 includes 1.0, 1.5, 2.0, 2.75, 3.0, 3.80, 4.0, 5.0, etc.).

As discussed herein, the process of the present disclosure provides a process for regenerating a titanium silicalite catalyst fouled during the reaction between the olefin and the peroxide compound to produce the oxirane. For one or more embodiments, the process includes contacting the fouled titanium silicalite catalyst with the regeneration solution including at least one oxidizing agent to provide the regenerated titanium silicalite catalyst. In an alternative embodiment, the process includes contacting the fouled titanium silicalite catalyst with the regeneration solution including at least one oxidizing agent and further including at least one organic compound to provide the regenerated titanium silicalite catalyst.

For one or more embodiments, the oxidizing agent can be selected from the group consisting of hydrogen peroxide, ozone, organic peroxide compounds, inorganic peroxide compounds, and combinations thereof. The oxidizing agent is preferably an oxidizing agent that is used in the epoxidation reaction where the titanium silicalite catalyst became fouled. In one embodiment, the oxidizing agent is hydrogen peroxide.

For one or more embodiments, the regeneration solution can have an oxidizing agent concentration of less than 0.50 wt % based on a total weight of the regeneration solution. For one or more embodiments, the regeneration solution can have an oxidizing agent concentration within a range of from 0.10 wt % to 0.49 wt %, preferably within a range of from 0.2 wt % to 0.47 wt %, and more preferably within a range of from 0.2 wt % to 0.45 wt %.

For one or more embodiments, the process includes adjusting a pH of the regeneration solution to less than 2 prior to contacting the fouled titanium silicalite catalyst with the regeneration solution. In one embodiment, the pH of the regeneration solution is adjusted to 1 or less. For example, an acid can be added to the regeneration solution to adjust the pH of the regeneration solution. Examples of acids that can be used to adjust the pH include, but are not limited to, sulfuric acid, hydrochloric acid, phosphoric acid, acetic acid, and combinations thereof. In one embodiment, the pH of the regeneration solution is adjusted by adding sulfuric acid. Additionally, the pH of the regeneration solution can be adjusted by contact with ion exchange resins, supported acids and bases, organic acids, buffers, or combinations thereof.

For one or more embodiments, the regeneration solution can include a reaction effluent from the epoxidation reaction between the olefin and the peroxide compound. The reaction effluent arising from the epoxidation reaction may contain an amount of the oxidizing agent, which was not consumed during the epoxidation. For the embodiments, an oxidizing agent can be added to the reaction effluent to provide the effluent with an oxidizing agent concentration of less than 0.50 wt % based on a total weight of the regeneration solution, exclusive of the titanium silicalite catalyst. The oxidizing agent added to the reaction effluent can be selected from the oxidizing agents discussed herein. For one or more embodiments, the oxidizing agent added to the reaction effluent can be the oxidizing agent used in the epoxidation reaction (e.g., hydrogen peroxide). For one or more embodiments, a pH of the reaction effluent can be adjusted to less than 2 prior to contacting the fouled titanium silicalite catalyst with the regeneration solution. The pH of the effluent can be adjusted by the methods discussed herein.

For one or more embodiments, regenerating the titanium silicalite catalyst fouled during the epoxidation reaction can be performed in situ. As one skilled in the art can appreciate, the epoxidation reaction can occur in a batch process, semi-batch process, or continuous process. As such, there are a number of types of vessels and configurations of vessels to carry out the epoxidation reaction. For example, the titanium silicalite catalyst of the epoxidation reaction can be in a slurry with the olefin and peroxide compound to form the reaction mixture. Additionally, the titanium silicalite catalyst can be in a fixed-bed configuration in the reaction mixture.

For one or more embodiments, contacting the fouled titanium silicalite catalyst with the regeneration solution can include passing the regeneration solution through the vessel (e.g., fixed-bed reactor) in which the titanium silicalite catalyst is situated during the epoxidation reaction. Additionally, the titanium silicalite catalyst can be removed from the vessel where the epoxidation reaction occurred and treated separately and returned to the vessel once regenerated for a subsequent epoxidation reaction. The regeneration solution can be introduced continuously or non-continuously (e.g., by successive introductions of several doses of oxidizing agent) during the regeneration. Additionally, the regeneration solution can be added in one introduction. Contacting the fouled titanium silicalite catalyst can include mixing or stirring the regeneration solution with the fouled titanium catalyst. For one or more embodiments, regenerating the titanium silicalite catalyst is carried out within a temperature range of 0° C. to 100° C., preferably within a range of from 60° C. to 100° C., and more preferably within a range of from 75° C. to 100° C.

For one or more embodiments, the regenerated catalyst can be washed in a washing step. The washing step can include bringing a catalyst undergoing regeneration, i.e., a fouled and/or regenerated catalyst, into contact with an organic compound. Examples of the organic compound include, but are not limited to, aliphatic, cyclic, aromatic, halogenated, supercritical, or alcoholic organic diluents. Water could be used alternatively. For one embodiment, the organic compound is methanol. For one or more embodiments, the catalyst undergoing regeneration is washed for a time period within a range of from 5 minutes to 60 minutes, preferably 30 minutes.

Embodiments of the present disclosure further provide a process for regenerating the titanium silicalite catalyst fouled during the reaction between the olefin and the peroxide by contacting the fouled titanium silicalite catalyst with a regeneration solution having a pH of less than 2 and at least one oxidizing agent. For the embodiments, the regeneration solution can have an oxidizing agent concentration within a range of from 0.10 wt % to 2.0 wt %, preferably within a range of from 0.2 wt % to 1.0 wt %, and more preferably within a range of from 0.3 wt % to 0.5 wt % based on the total weight of the regeneration solution, exclusive of the titanium silicalite catalyst. In one embodiment, the oxidizing agent concentration of the regeneration solution having a pH of less than 2 is 1 wt %, based on the total weight of the regeneration solution, exclusive of the titanium silicalite catalyst. For one or more embodiments, the oxidizing agent can be selected from the oxidizing agents discussed herein. Similarly, the pH of the regeneration solution can be adjusted as described herein.

For one or more embodiments, the regeneration solution can include additional materials. Examples include, but are not limited to iron ions and other metals.

For the embodiments of the present disclosure, the process applies to fouled catalysts of titanium silicalite type, and in particular to those used in a reaction between an olefin and a peroxide compound in the presence of a solvent mixture with an alcohol and a non-reactive co-solvent to form an oxirane (e.g., reacting allyl chloride with hydrogen peroxide to form epichlorohydrin). Catalysts used in epoxidation reactions can be selected from heterogeneous catalysts which comprise a porous oxide material such as zeolite. As appreciated, zeolites are solid containing silicas which have microporous crystalline ordered channels with a cage structure and pore openings. Along with microporous zeolites, mesoporous and macroporous zeolite type catalysts can also be used. For the embodiments, the catalyst is preferably selected from titanium-silicalites generally known as TS-1 having a MFI structure. It is also possible to use titanium-silicalites with a MEL or intermediate MFI/MEL structure and titanium-silicalites from beta zeolites containing titanium and having a BEA structure. Other titanium containing zeolite catalysts generally known as TS-2, TS-3, ZSM-48 and ZMS-12 can also be used.

For the embodiments, a portion or all of the titanium in the zeolite catalyst can be replaced by, but not limited to, boron, aluminum, iron, gallium, vanadium, zirconium, chromium, niobium or a mixture of two or more thereof. Additional examples of zeolites containing titanium, vanadium, chromium, niobium, and zirconium include, but are not limited to, BEA, MOR, TON, MTW, FER, CHA, ERI, RHO, GIS, BOG, NON, EMT, HEU, KFI, FAU, DDR, MTT, RUT, RTH, LTL, MAX, GME, NES, OFF, SGT, EUO, MFS, MWW and ITQ-4. It is also possible to use titanium-containing zeolites having the UTD-1, CIT-1 or CIT-5 structure in the process of the present disclosure. Furthermore, other heterogeneous and homogeneous catalysts may be used. Examples include, but are not limited to, soluble metal catalysts such as ligand-bound rhenium, tungsten, and manganese, along with the heterogenized forms of these.

For example, in a non-fixed bed reactor configuration, the catalyst can be used within a range of from 0.1 wt % to 30 wt %, more preferably within a range of from 0.1 wt % to 15 wt %, and still more preferably within a range of from 0.1 wt % to 5 wt %, based on the weight of the reaction mixture.

For one or more embodiments, the olefin can be selected from the group consisting of linear and/or branched acyclic or cyclic aliphatic or aromatic olefins, including those which may contain multiple double bonds. Additional examples of the olefin include, but are not limited to, chloride-butadiene and other linear dialkenes, cyclohexene and other cyclic alkenes and dialkenes, substitute alkenes, such as halogenated alkenes, styrene, divinylbenzene, dicyclopentadiene, other aromatic alkenes and mixtures thereof. Moreover, butenes, pentenes, hexenes, octenes, heptenes, 1-tridecene, mesityl oxide, isoprene, cyclo-octane, cyclohexene or bicyclic compounds such as norbornenes or pinenes may also be used. In one embodiment, the olefin is allyl chloride.

The olefin can be used in a range of from 10 weight percent (wt %) to 90 wt %, preferably 20 wt % to 80 wt %, more preferably 30 wt % to 70 wt %, and still more preferably 40 wt % to 65 wt %, based on a total weight of a reaction mixture. For example, in a fixed bed reactor configuration, the total weight of the reaction mixture includes the olefin, peroxide compound and solvent mixture with the alcohol and the non-reactive co-solvent. In a non-fixed bed reactor configuration, the total weight of the reaction mixture includes the olefin, peroxide compound, catalyst and solvent mixture with the alcohol and the non-reactive co-solvent.

As discussed herein, the epoxidation reaction includes reacting the olefin with a peroxide compound. A "peroxide compound" refers to a compound containing one or more peroxide (—O—O—) functionalities, including organic or inorganic peroxides, peroxide adducts, or peracids. The peroxide compound can include, for example, but is not limited to, hydrogen peroxide, urea-hydrogen peroxide adduct, peracetic acid and mixtures thereof. Additional examples of peroxide compounds may include tert-butyl hydroperoxide and ethylbenzene hydroperoxide. For one or more embodiments, the peroxide compound is a hydrogen peroxide in solution. However, as one skilled in the art would appreciate, other organic and/or inorganic hydroperoxides may be used for the production of the oxirane. Examples of other hydroperoxides that may be used include, but are not limited to, tert-butyl hydroperoxide, ethylbenzene hydroperoxide, acetyl peroxide, benzoyl peroxide, methyl ethyl ketone peroxide, cumene peroxide and combinations thereof.

The peroxide compound can be used in a range of from 1 wt % to 35 wt %, preferably 1 wt % to 20 wt %, more preferably 1 wt % to 15 wt %, and still more preferably 1 wt % to 10 wt %, based on the total weight of the reaction mixture. As discussed above, the total weight of the reaction mixture in a fixed bed reactor configuration includes the olefin, peroxide compound and solvent mixture with the alcohol and the non-reactive co-solvent. In a non-fixed bed reactor configuration, the total weight of the reaction mixture includes the olefin, peroxide compound, catalyst and solvent mixture with the alcohol and the non-reactive co-solvent.

In one preferred embodiment of the present disclosure, an aqueous solution of hydrogen peroxide at about 30 wt % may be used such that the total amount of molecular hydrogen peroxide may be from about 1 wt % to about 7 wt %, based on the weight of the total reaction mixture.

As discussed herein, the epoxidation reaction is carried out in the presence of the solvent mixture with the alcohol and non-reactive co-solvents. The alcohol can be selected from protic solvents. For example, alcohols, such as methanol, ethanol, isopropyl alcohol, tert-butyl alcohol and cyclohexanol, can be used. For the embodiments, the solvent is preferably methanol. Mixtures of the various alcohols may also be used.

For the embodiments, the amount of the protic solvent in the reaction mixture can be within a range of from 0.5 wt % to 90 wt %, more preferably within a range of from 0.5 wt % to 50 wt %, and still more preferably within a range of from 1 wt % to 10 wt %, based on the total weight of the reaction mixture. As discussed above, the total weight of the reaction mixture in a fixed bed reactor configuration includes the olefin, peroxide compound and solvent mixture with the alcohol and the non-reactive co-solvent. In a non-fixed bed reactor configuration, the total weight of the reaction mixture includes the olefin, peroxide compound, catalyst and solvent mixture with the alcohol and the non-reactive co-solvent.

For the embodiments, the non-reactive co-solvent can be selected from non-water soluble solvents that include, but are not limited to, linear and cyclic alkanes of $C_3$-$C_{18}$, halogenated hydrocarbons, deactivated aromatics, amides, solvents containing nitriles, alcohols, and halogenated alcohols or mixtures thereof. Examples of the non-reactive co-solvent include, but are not limited to, carbon tetrachloride, propyl chloride, chloroform, dichloromethane, dichloroethane, hexane, octane, decalin, perfluorodecalin, mono or poly-chlorinated benzenes, mono- or poly-brominated benzenes, acetophenone, benzonitrile, acetonitrile, tritolyl phosphate, trichlorotrifluoroethane, trichloroethanol, trifluoroethanol or mixtures thereof. For the embodiments, the non-reactive co-solvent is preferably 1,2-dichlorobenzene.

The non-reactive co-solvent can be used within in a range of from 5 wt % to 70 wt %, more preferably within a range of from 10 wt % to 65 wt %, and still more preferably within a range of from 25 wt % to 55 wt %, based on the total weight of the reaction mixture. As discussed above, the total weight of the reaction mixture in a fixed bed reactor configuration includes the olefin, peroxide compound and solvent mixture with the alcohol and the non-reactive co-solvent. In a non-fixed bed reactor configuration, the total weight of the reaction mixture includes the olefin, peroxide compound, catalyst and solvent mixture with the alcohol and the non-reactive co-solvent.

As discussed above, one or more embodiments of the process of the present disclosure includes subjecting the catalyst undergoing regeneration to a washing step. Alternative embodiments of the process of the present disclosure eliminate the washing step, i.e., the catalyst is not contacted with a washing solution pre-regeneration and/or post-regeneration. Instead, the titanium silicalite catalyst is contacted with a regeneration solution that comprises at least one oxidizing agent and an organic compound. It was surprisingly discovered that it is possible to regenerate a titanium silicalite catalyst by treating a silicalite catalyst with a regeneration solution comprising at least one oxidizing agent and further comprising an organic compound, thereby eliminating the step(s) of pre- and/or post-regeneration wash. For example, the regeneration solution can include an oxidizing agent concentration of 0.5 to 5 weight percent (wt %) based on a total weight of the regeneration solution, exclusive of the titanium silicalite catalyst; and an organic compound at 5 to 95 weight percent (wt %) based on a total weight of the regeneration solution, exclusive of the titanium silicalite catalyst.

All of the U.S. patents, U.S. patent application publications, U.S. patent applications, foreign patents, foreign patent applications and non-patent publications referred to in this specification are incorporated herein by reference, in their entirety.

From the foregoing it will be appreciated that, although specific embodiments of the disclosure have been described herein for purposes of illustration, various modifications may be made without deviating from the spirit and scope of the disclosure.

EXAMPLES

The following examples are given to illustrate, but not limit, the scope of this disclosure.

Materials

Catalyst, titanium silicalite (TS-1), available from Süd-Chemie.

Olefin, allyl chloride (99.4% purity), obtained from The Dow Chemical Company.

Peroxide compound, hydrogen peroxide solution (30-50 wt %/aq), available from VWR.

Oxidizing agent, hydrogen peroxide solution (30-50 wt %/aq), available from VWR.

Alcohol, Methanol, available from Fisher Scientific.

Non-reactive co-solvent, 1,2-dichlorobenzene, available from Sigma Aldrich.

Test Methods pH Measurement

The pH was measured on a Beckman model 35 pH meter using an Orion 8272BN combination electrode with 2M potassium chloride filling solution, calibrated daily with pH=4 and pH=7 buffers.

Gas Chromatography (GC)

The amount of organic components remaining in samples was determined by analysis on a Hewlett Packard 6890 series G1530A gas chromatography with a Hewlett Packard 7682 series injector and flame ionization detector.

Hydrogen Peroxide Titration

Peroxide amounts were analyzed by iodometric titration using 0.01N sodium thiosulfate. The peroxide concentration may be calculated as follows: ppm $H_2O_2$=(milliliters titrant used) (0.01 N)(17000)/gram sample. Titrations were performed using a Mettler Toledo DL5x V2.3 titrator with a DM140 sensor.

Epichlorohydrin (Epi) Yield

The epichlorohydrin yield is determined by taking the amount of Epi produced during epoxidation reaction/theoretical maximum amount of Epi produced at 100% $H_2O_2$ conversion to Epi.

Titanium Silicalite (TS-1) Catalysts Used in Examples 1-3 and Comparative Example A In Examples 1-3 and Comparative Example A, three different states of the TS-1 catalyst are utilized: (1) fresh TS-1 catalyst, (2) fouled TS-1 catalyst, and (3) regenerated TS-1 catalyst. A fresh TS-1 catalyst is a dry catalyst from a vendor. For the purposes of Examples 1-3 and Comparative Example A, a fouled TS-1 catalyst is a catalyst that has been used continuously in an epoxidation reaction for approximately 70 hours and then partially dried in a vacuum oven at 60° C. for 15 minutes and contains 30 wt % of other components, based on a total weight of the partially dried TS-1 catalyst. For the purposes of Examples 1-3 and Comparative Example A, a regenerated TS-1 catalyst is a TS-1 catalyst that has been regenerated and then partially dried in a vacuum oven at 60° C. for 15 minutes and contains 30 wt % of other components, based on a total weight of the regenerated TS-1 catalyst. The amount of material remaining in the fouled and regenerated TS-1 catalysts was determined by measuring the weight lost after further calcining said catalysts at 600° C. for approximately 2 or more hours.

(1) Epoxidation Using a Fresh TS-1 Catalyst

Allyl chloride (52.3 wt %), methanol (5.2 wt %), 1,2-dichlorobenzene (23.2 wt %), and fresh TS-1 catalyst (1.4 wt %) were added to a 750-mL jacketed glass reactor with a stainless steel cooling coil, thermocouple, mechanical stirrer, addition funnel, $N_2$ purge with gas scrubber, and reflux condenser/cold finger combination. The contents of the reactor were brought to 25.5° C. After the reactor contents were brought to 25.5° C., a peroxide compound (30 wt %/aq. hydrogen peroxide, 17.9 wt % total solution, 5.3 wt % $H_2O_2$) was added to the addition funnel to form a reaction mixture. The reaction mixture was stirred at 600 rpm, and the reaction mixture was maintained at approximately 40° C. using the cooling coil. After 60 minutes the reactor mixture was drained equally into two 250 mL centrifuge tubes, and then centrifuged at 10,000 rpm and 0° C. for 10 minutes. The liquid was decanted from the regenerated TS-1 catalyst into a separatory funnel and allowed to separate into a liquid organic phase and a liquid aqueous phase. The liquid organic phase and the liquid aqueous phase were analyzed by GC and the amount of peroxide remaining in each phase was determined by iodometric titration with sodium thiosulfate. The Epi Yield was calculated and is shown Table I.

(2) Epoxidation Using a Fouled TS-1 Catalyst

Allyl chloride (52.0 wt %), methanol (5.2 wt %), 1,2-dichlorobenzene (23.0 wt %), and a fouled TS-1 catalyst (2.0 wt %, equivalent to 7.8 g fresh TS-1 catalyst) were added to a 750-mL jacketed glass reactor with a stainless steel cooling coil, thermocouple, mechanical stirrer, addition funnel, $N_2$ purge with gas scrubber, and reflux condenser/cold finger combination. The contents of the reactor were brought to 25.5° C. After the reactor contents were brought to 25.5° C., a peroxide compound (30 wt %/aq. hydrogen peroxide, 17.8 wt % total solution, 5.3 wt % $H_2O_2$) was added to the addition funnel to form a reaction mixture. The reaction mixture was stirred at 600 rpm, and the reaction mixture was maintained at approximately 40° C. using the cooling coil. After 60 minutes the reactor mixture was drained equally into two 250 mL centrifuge tubes, and then centrifuged at 10,000 rpm and 0° C. for 10 minutes.

The liquid was decanted from the regenerated TS-1 catalyst into a separatory funnel and allowed to separate into a liquid organic phase and a liquid aqueous phase. The liquid organic phase and the liquid aqueous phase were analyzed by GC and the amount of peroxide remaining in each phase was determined by iodometric titration with sodium thiosulfate. The Epi Yield was calculated and is shown Table I.

TABLE I

| Catalyst Used in Epoxidation | Epi Yield |
| --- | --- |
| Fresh TS-1 | 89.7% |
| Fouled TS-1 | 86.3% |

Table I illustrates the decrease in activity of the TS-1 catalyst. As seen in Table 1, a fresh TS-1 catalyst produces an epi yield of 89.7% whereas the fouled TS-1 catalyst produces an epi yield of 86.3%.

Regenerated TS-1 Catalysts of Examples 1-3

Examples 1-3 illustrate various embodiments for regenerating a TS-1 catalyst. Example 1 illustrates regenerating a fouled TS-1 catalyst by using a regeneration solution having an oxidizing agent concentration of 0.45 wt %, based on a total weight of the regeneration solution. Example 2 illustrates regenerating a fouled TS-1 catalyst by using a regeneration solution having an oxidizing agent concentration of 0.45 wt %, based on a total weight of the regeneration solution and a pH of 1. Example 3 illustrates regenerating a fouled TS-1 catalyst by using an effluent of an epoxidation reaction having an oxidizing agent concentration of 0.45 wt %, based on a total weight of the regeneration solution.

Example 1

Regenerated TS-1 Catalyst 1

A fouled TS-1 catalyst (10.2 g, equivalent to 7.8 g fresh TS-1) was added to a 750-mL jacketed glass reactor with a stainless steel cooling coil, thermocouple, mechanical stirrer, addition funnel, $N_2$ purge with gas scrubber, and reflux condenser/cold finger combination. A regeneration solution (349.6 g) having an oxidizing agent concentration of 0.45 wt % (hydrogen peroxide in water) was added to the reactor to from a mixture. The mixture was stirred at 600 revolutions per minute (rpm) and maintained at approximately 80° C. using the cooling coil. After 60 minutes the mixture was drained from the reactor into two 250 mL centrifuge tubes, and then centrifuged at 10,000 rpm at 0° C. for 10 minutes.

The regeneration solution was decanted from the regenerated TS-1 catalyst and the amount of peroxide remaining in the regeneration solution was determined by iodometric titration with sodium thiosulfate. The regenerated TS-1 catalyst was stirred with methanol (350 g) at ambient temperature (23° C.). After 30 minutes the mixture was divided into two 250 mL centrifuge tubes, and then centrifuged at 10000 rpm at 0° C. for 10 minutes. The regenerated TS-1 catalyst was recovered by decantation and dried in a vacuum oven at 60° C. for 15 minutes.

Example 2

Regenerated TS-1 Catalyst 2

A fouled TS-1 catalyst (10.2 g, equivalent to 7.8 g fresh TS-1) was added to a 750-mL jacketed glass reactor with a stainless steel cooling coil, thermocouple, mechanical stirrer, addition funnel, $N_2$ purge with gas scrubber, and reflux condenser/cold finger combination. A pH of a regeneration solution having an oxidizing agent concentration of 1 wt % (hydrogen peroxide in water) based on the total weight of the regeneration solution was adjusted to 1 by adding sulfuric acid ($H_2SO_4$) (2.8 g). The pH adjusted regeneration solution (347.0 g) had an oxidizing agent concentration of 0.98 wt % based on the total weight of the regeneration solution was added to the reactor to from a mixture. The mixture was stirred at 600 revolutions per minute (rpm), and the mixture was maintained at approximately 80° C. using the cooling coil. After 60 minutes the mixture was drained from the reactor into two 250 mL centrifuge tubes, and then centrifuged at 10000 rpm at 0° C. for 10 minutes.

The regeneration solution was decanted from the regenerated TS-1 catalyst and the amount of peroxide remaining in the regeneration solution was determined by iodometric titration with sodium thiosulfate. The regenerated TS-1 catalyst was stirred with methanol (350 g) at ambient temperature. After 30 minutes the mixture was divided into two 250 mL centrifuge tubes, and then centrifuged at 10000 rpm at 0° C. for 10 minutes. The regenerated TS-1 catalyst was recovered by decantation and dried in a vacuum oven at 60° C. for 15 minutes.

Example 3

Regenerated TS-1 Catalyst 3

A fouled TS-1 catalyst (10.2 g, equivalent to 7.8 g fresh TS-1) was added to a 750-mL jacketed glass reactor with a stainless steel cooling coil, thermocouple, mechanical stirrer, addition funnel, $N_2$ purge with gas scrubber, and reflux condenser/cold finger combination. An oxidizing agent 30 wt % $H_2O_2$ (1.17 g) was added to an aqueous effluent (79.02 g; composition:=21.4 wt % methanol, 0.012 wt % allyl chloride, 0.018 wt % allyl alcohol, 0.26 wt % epichlorohydrin, 0.16 wt % 1-chloro-3-methoxy-2-hydroxy propane, 0.052 wt % 1,2-dichlorobenzene, 0.39 wt % 1-chloro-2,3-dihydroxy propane, and 77.7 wt % water) to form a regeneration solution having an oxidizing concentration of 0.45 wt %, based on a total weight of the regeneration solution. The regeneration solution (80.19 g) was added to the reactor to form a mixture. The mixture was stirred at 600 rpm, and the mixture was maintained at approximately 80° C. using the cooling coil. After 60 minutes the mixture was drained from the reactor into two 250 mL centrifuge tubes, and then centrifuged at 10000 rpm at 0° C. for 10 minutes.

The regeneration solution was decanted from the regenerated TS-1 catalyst and analyzed by GC. The amount of peroxide remaining in the regeneration solution was determined by iodometric titration with sodium thiosulfate. The regenerated TS-1 catalyst was stirred with methanol (350 g) at ambient temperature. After 30 minutes the mixture was divided into two 250 mL centrifuge tubes, and then centrifuged at 10000 rpm at 0° C. for 10 minutes. The regenerated TS-1 catalyst was recovered by decantation and dried in a vacuum oven at 60° C. for 15 minutes.

Epoxidation Reactions Using Regenerated TS-1 Catalysts from Examples 1-3

To illustrate the utility of the process of the present disclosure the regenerated TS-1 catalysts from Examples 1-3 were used in an epoxidation to form ephichlorhydrin (Epi).

The epichlorohydrin yield (i.e., amount of Epi produced during epoxidation reaction/theoretical maximum amount of Epi produced at 100% $H_2O_2$ conversion to Epi), was determined for each example.

Epoxidation Reaction Using the Regenerated TS-1 Catalyst from Example 1

Allyl chloride (52.0 wt %), methanol (5.2 wt %), 1,2-dichlorobenzene (23.0 wt %), and the regenerated TS-1 catalyst from Example 1 (2.00 wt %, equivalent to 1.55 wt % fresh catalyst) were added to a 750-mL jacketed glass reactor with a stainless steel cooling coil, thermocouple, mechanical stirrer, addition funnel, $N_2$ purge with gas scrubber, and reflux condenser/cold finger combination. The contents of the reactor were brought to 25.5° C. After the reactor contents were brought to 25.5° C., a peroxide compound (30 wt %/aq. hydrogen peroxide, 17.8 wt % total solution, 5.3 wt % $H_2O_2$) was added to the addition funnel to form a reaction mixture. The reaction mixture was stirred at 600 rpm, and the reaction mixture was maintained at approximately 40° C. using the cooling coil. After 60 minutes the reactor mixture was drained equally into two 250 mL centrifuge tubes, and then centrifuged at 10000 rpm and 0° C. for 10 minutes.

The liquid was decanted from the regenerated TS-1 catalyst into a separatory funnel and allowed to separate into a liquid organic phase and a liquid aqueous phase. The liquid organic phase and the liquid aqueous phase were analyzed by GC and the amount of peroxide remaining in each phase was determined by iodometric titration with sodium thiosulfate. The Epi Yield was calculated and is shown Table II.

Epoxidation Reaction Using the Regenerated TS-1 Catalyst from Example 2

Allyl chloride (52.0 wt %), methanol (5.2 wt %), 1,2-dichlorobenzene (23.0 wt %), and the regenerated TS-1 catalyst from Example 2 (2.00 wt %, equivalent to 1.55 wt % fresh catalyst) were added to a 750-mL jacketed glass reactor with a stainless steel cooling coil, thermocouple, mechanical stirrer, addition funnel, $N_2$ purge with gas scrubber, and reflux condenser/cold finger combination. The contents of the reactor were brought to 25.5° C. After the reactor contents were brought to 25.5° C., a peroxide compound (30 wt %/aq. hydrogen peroxide; 17.8 wt % total solution, 5.3 wt % $H_2O_2$) was added to the addition funnel to form a reaction mixture. The reaction mixture was stirred at 600 rpm, and the reaction mixture was maintained at approximately 40° C. using the cooling coil. After 60 minutes the reactor mixture was drained equally into two 250 mL centrifuge tubes, and then centrifuged at 10000 rpm and 0° C. for 10 minutes.

The liquid was decanted from the regenerated TS-1 catalyst into a separatory funnel and allowed to separate into a liquid organic phase and a liquid aqueous phase. The liquid organic phase and the liquid aqueous phase were analyzed by GC and the amount of peroxide remaining in each phase was determined by iodometric titration with sodium thiosulfate. The Epi Yield was calculated and is shown Table II.

Epoxidation Reaction Using the Regenerated TS-1 Catalyst from Example 3

Allyl chloride (51.9 wt %), methanol (5.2 wt %), 1,2-dichlorobenzene (23.0 wt %), and regenerated TS-1 catalyst from Example 2 (2.03 wt %, equivalent to 1.56 wt % fresh catalyst) were added to a 750-mL jacketed glass reactor with a stainless steel cooling coil, thermocouple, mechanical stirrer, addition funnel, $N_2$ purge with gas scrubber, and reflux condenser/cold finger combination. The contents of the reactor were brought to 25.5° C. After the reactor contents were brought to 25.5° C., a peroxide compound (30 wt %/aq. hydrogen peroxide; 17.8 wt % total solution, 5.3 wt % $H_2O_2$) was added to the addition funnel to form a reaction mixture. The reaction mixture was stirred at 600 rpm, and the reaction mixture was maintained at approximately 40° C. using the cooling coil. After 60 minutes the reactor mixture was drained equally into two 250 mL centrifuge tubes, and then centrifuged at 10000 rpm and 0° C. for 10 minutes.

The liquid was decanted from the regenerated TS-1 catalyst into a reparatory funnel and allowed to separate into a liquid organic phase and a liquid aqueous phase. The liquid organic phase and the liquid aqueous phase were analyzed by GC and the amount of peroxide remaining in each phase was determined by iodometric titration with sodium thiosulfate. The Epi Yield was calculated and is shown Table II.

TABLE II

| Example | Epi Yield |
| --- | --- |
| Example 1 | 89.8% |
| Example 2 | 88.9% |
| Example 3 | 87.5% |

Comparing the results of Table II with Table I it can be seen that the regenerated TS-1 catalyst of Example 1 gave approximately the same Epi yield as the fresh TS-1 catalyst. Similarly, the regenerated TS-1 catalyst from Example 2 gave slightly lower Epi yield results than the fresh TS-1 catalyst. Finally, the regenerated TS-1 catalyst from Example 3 gave approximately a 2% lower Epi yield than the fresh TS-1 catalyst. However, the Epi yield of Examples 1-3 was within 2% and 1% higher than the fouled TS-1 catalyst. As one skilled in the art will appreciate, saving 1% of epichlorohydrin can save a significant amount of money when applied to a full-scale manufacturing plant.

Comparative Example A

A fouled TS-1 catalyst (10.12 g, equivalent to 7.8 g fresh TS-1) was added to a 750-mL jacketed glass reactor with a stainless steel cooling coil, thermocouple, mechanical stirrer, addition funnel, $N_2$ purge with gas scrubber, and reflux condenser/cold finger combination. A pH of a regeneration solution having an oxidizing agent concentration of 1 wt % (hydrogen peroxide in water), based on the total weight of the regeneration solution, was adjusted to 6.9 by adding sodium hydroxide (NaOH). The pH adjusted regeneration solution (351.36 g) was added to the reactor to form a mixture. The mixture was stirred at 600 revolutions per minute (rpm), and the mixture was maintained at approximately 80° C. using the cooling coil. After 60 minutes the mixture was drained from the reactor into two 250 mL centrifuge tubes, and then centrifuged at 10000 rpm at 0° C. for 10 minutes.

The regeneration solution was decanted from the regenerated TS-1 catalyst and the amount of peroxide remaining in the regeneration solution was determined by iodometric titration with sodium thiosulfate. The regenerated TS-1 catalyst was stirred with methanol (350 g) at ambient temperature. After 30 minutes the mixture was divided into two 250 mL centrifuge tubes, and then centrifuged at 10000 rpm at 0° C. for 10 minutes. The regenerated TS-1 catalyst was recovered by decantation and dried in a vacuum oven at 60° C. for 15 minutes.

Epoxidation Reaction Using the Regenerated TS-1 Catalyst from Comparative Example A Allyl chloride (52.1 wt %), methanol (5.2 wt %), 1,2-dichlorobenzene (23.2 wt %), and the regenerated TS-1 catalyst from Comparative Example A (1.7 wt %, equivalent to 1.36 wt % fresh catalyst) were added to a 750-mL jacketed glass reactor with a stainless steel cooling coil, thermocouple, mechanical stirrer, addition funnel, $N_2$ purge with gas scrubber, and reflux condenser/cold finger combination. The contents of the reactor were brought to 25.5° C. After the reactor contents were brought to 25.5° C., a peroxide compound (30 wt %/aq. hydrogen peroxide; 17.8 wt % total solution, 5.3 wt % $H_2O_2$) was added to the addition funnel to form a reaction mixture. The reaction mixture was stirred at 600 rpm, and the reaction mixture was maintained at approximately 40° C. using the cooling coil. After 60 minutes the reactor mixture was drained equally into two 250 mL centrifuge tubes, and then centrifuged at 10000 rpm and 0° C. for 10 minutes. The liquid was decanted from the TS-1 catalyst into a reparatory funnel and allowed to separate into a liquid organic phase and a liquid aqueous phase. The liquid organic phase and the liquid aqueous phase were analyzed by GC. The amount of peroxide remaining in each phase was determined by iodometric titration with sodium thiosulfate. The Epi Yield was calculated and is shown Table III.

TABLE III

| Comparative Example | Epi Yield |
| --- | --- |
| Comparative Example A | 83.8% |

Comparing the results of Table III with Table I it can be seen that the regenerated TS-1 catalyst of Comparative Example A gave a significantly lower Epi yield than the fresh TS-1 catalyst. For example, the Comparative Example A Epi yield was approximately 5% lower than the fresh TS-1 catalyst. Additionally, comparing the Epi yield of the Comparative Example A with Examples 1-3, the Epi yield of the Comparative Example is lower than each Example 1 through 3.

Additionally, the Epi Yield of Comparative Example A is lower than the fouled TS-1 catalyst in Table I. It is known by those skilled in the art that residual NaOH left in the TS-1 catalyst pores can reduce the yield of epichlorohydrin. It is believed that the sodium ions ($Na^+$) can stabilize an active site of the TS-1 catalyst making it less reactive with the olefin such as allyl chloride. Additionally, the hydroxide ions ($OH^-$) can react with the epichlorohydrin produced and form 1-chloro-2,3-dihydroxy propane, which also reduces the yield of epichlorohydrin.

Comparative Example B, Examples 4-5

In Comparative Example B and Examples 4 and 5, three different states of the TS-1 catalyst are utilized: (1) fresh, (2) fouled, and (3) regenerated catalyst. For the purposes of Comparative Example B and Examples 4 and 5, a fresh TS-1 catalyst is a commercially available dry TS-1 catalyst, e.g., TS-1 beads of 1.6 to 2.5 mm particle size. Inert glass beads filled the space above and below the catalyst in the reactor. For purposes of Comparative Example B and Examples 4-5, a fouled TS-1 catalyst is a TS-1 catalyst that has been used continuously in an epoxidation reaction for approximately 20 hours and/or the Epi productivity has decreased by more than 25% of its maximum value. The "maximum value" for a TS-1 catalyst can be determined experimentally by methods known to the art, for example, by use of an epi productivity plot of a fresh or regenerated catalyst, e.g., the maximum value is the point at which the slope of the epi productivity curve changes from positive to negative. For the purposes of Comparative Example B and Examples 4 and 5, a regenerated TS-1 catalyst is a TS-1 catalyst that has been regenerated with a particular regeneration solution of interest and at an operating temperature of approximately 80° C. for more than 5 hours.

Comparative Example B $H_2O_2$ and Water Regeneration

Epoxidation Reaction. 150.1 g of fresh TS-1 catalyst (TS-1 beads; 1.6-2.5 mm), were placed in a 1.05" ID×49.125" long open tube reactor equipped with a recirculation loop (total volume of loop ~46 mL). The reactor was feed continuously (about 20 hours) with an aqueous (43 wt % $H_2O_2$ solution) feed rate of 1.0 mL/min and organic (6.35 wt % MeOH, 50.3 wt % Allyl Chloride, 42.9 wt % o-DCB mixture) feed rate of 5.0 mL/min with a recycle rate of 2.0 L/min. The reactor operated at 40° C.

The reactor contents (liquid contents only, catalyst remained in reactor) were then emptied and blown down with nitrogen to remove the bulk of the reaction mixture prior to introduction of the regeneration solution. The operating temperature was 80° C. The regeneration process was done batch-wise and did not utilize methanol in the solution. No washing step was performed. After the regeneration process, the reactants were fed back at the same conditions mentioned above. For each regeneration solution batch, it was allowed that the initial $H_2O_2$ concentration was depleted to about 0.1 wt % before introducing a new batch with higher a $H_2O_2$ concentration.

Table IV shows the epi productivity, epi selectivity and $H_2O_2$ concentration in the effluent at three different time periods using the fresh TS-1 catalyst. In particular, after one hour of operation the first sample was analyzed. After 5 hours of operation, when the Epi productivity reached a maximum amount, the second sample was analyzed. After 20 hours of operation, when a steady state was reached, the third sample was analyzed.

TABLE IV

| | Fresh TS-1 Catalyst | | |
|---|---|---|---|
| Hours of operation | Epi Production lbs/hr/ft³ cat | Epi selectivity % | $H_2O_2$ concentration in effluent Wt % |
| 1 | 1.5 | 95.2 | 0.4 |
| 5 | 16.9 | 90 | 7.4 |
| 20 | 6.9 | 88.2 | 25.4 |

Table V shows the starting $H_2O_2$ concentration for each of the five different regeneration solutions used during the regeneration process of Comparative Example 4(a), i.e., the concentration of $H_2O_2$ in the regeneration solution prior to contacting the fouled TS-1 catalyst with the regeneration solution.

TABLE V

| Batch Number | Starting $H_2O_2$ concentration of Comparative Regeneration solution Wt % |
|---|---|
| 1 | 1.07 |
| 2 | 1.04 |
| 3 | 1.29 |
| 4 | 1.56 |
| 5 | 1.54 |

Table VI shows the epi productivity, epi selectivity and $H_2O_2$ concentration in the effluent at three different time periods using the catalyst regenerated with the $H_2O_2/H_2O$ solutions under the similar epoxidation conditions as the TS-1 fresh catalyst. The first sample was analyzed after one hour of operation; the second sample was analyzed after 5 hours of operation when the Epi productivity reached a maximum amount; and the third sample was analyzed after 20 hours of operation when a steady state was reached.

TABLE VI

| TS-1 Catalyst regenerated with the $H_2O_2/H_2O$ solutions | | | |
|---|---|---|---|
| Hours of operation | Epi Productivity lbs/hr/ft³ cat | Epi selectivity % | $H_2O_2$ concentration in effluent Wt % |
| 1 | 3.2 | 91.7 | 0.7 |
| 5 | 9.9 | 83.6 | 15.5 |
| 20 | 7.3 | 79.6 | 25.1 |

In comparing Tables IV and VI, it can be seen that the epi productivity and $H_2O_2$ concentration in the effluent for the epoxidation reaction with fresh catalyst (Table IV) and the epoxidation reaction with $H_2O_2$/water solution (Table VI) remained about the same, see for example at the 20th hour of operation. However, the epi selectivity had a dramatic change. Regenerating with a solution of water and $H_2O_2$ yielded lower selectivity, and the productivity did not reach the same maximum as that of the fresh catalyst for the fifth hour of operation.

Example 4

$H_7O_2$/Water/Methanol Regeneration

The reactor contents (liquid contents, catalyst remained) were emptied (from the previous run, i.e., Comparative Example B) and blown down with nitrogen to remove the bulk of the reaction mixture prior to introduction of the regeneration solution. The operating temperature was 80° C. The regeneration process was done batch-wise with a total of 4 batches (each containing methanol). Each contained on average 1.4 wt % $H_2O_2$ and 15 wt % methanol as the starting composition. No washing step was performed. After the regeneration process, the reactants were fed back at the same conditions as in Comparative Example B. For each regeneration solution batch, the initial $H_2O_2$ concentration was depleted to about 0.1 wt % before introducing a new batch with a higher $H_2O_2$ concentration.

Table VII shows the epi productivity, epi selectivity and $H_2O_2$ concentration in the effluent at three different time periods using regenerated catalyst, i.e., the catalyst regenerated with the $H_2O_2$, water and methanol solution. In particular, after one hour of operation the first sample was analyzed. After 5 hours of operation, when the Epi productivity reached a maximum amount, the second sample was analyzed. After 11 hours of operation, the last sample was taken for this run.

TABLE VII

| Hours of operation | Description | Epi productivity Lbs/hr/ft³ cat | Epi selectivity % | $H_2O_2$ concentration in effluent |
|---|---|---|---|---|
| 1 | 1st sample | 1.24 | 21.5 | 0.5 |
| 5 | Epi peak | 11.5 | 84.3 | 10.1 |
| 11 | Last sample | 8.9 | 82.4 | 16.5 |

In comparing the results from the epoxidation reaction with fresh TS-1 catalyst and the regenerated TS-1 catalyst with $H_2O_2$/water solution (Tables IV and VI, respectively), and regenerated TS-1 catalyst with $H_2O_2$/water/methanol solution (Table VII), the methanol containing regeneration solution showed an improvement over the $H_2O_2$/water solution in Epi selectivity and Epi productivity (see, for example, the data for the 5$^{th}$ hour of operation).

Turning now to FIG. 1, the epi productivity, epi selectivity and $H_2O_2$ concentration in the effluent using the fresh catalyst, using the catalyst regenerated with the solution of water and $H_2O_2$, i.e., without methanol; and using the same catalyst regenerated with the regeneration solution of water, $H_2O_2$ and methanol are graphically depicted. FIG. 1 shows plotted data generated from Comparative Example B and Example 4, represented as follows: epi productivity by squares; $H_2O_2$ concentration in effluent by triangles; and epi selectivity by diamonds.

Example 5

$H_7O_2$, Water and Methanol Regeneration

Epoxidation Reaction. 150.0 g of fresh TS-1 catalyst (TS-1 beads; 1.6-2.5 mm) were placed in a 697 mL (1.05" ID×49.125" long; open tube) reactor equipped with a recirculation loop (total volume of loop 46 mL). The reactor was fed continuously (about 20 hours) with an aqueous (35 wt % $H_2O_2$ solution) feed rate of 1.0 mL/min and organic (6.2 wt % MeOH, 50.6 wt % Allyl Chloride, 42.8 wt % o-DCB mixture) feed rate of 5.0 mL/min with a recycle rate of 2.0 L/min. Reactor operated at 40° C.

The reactor contents (liquid contents, catalyst remained) were then emptied and blown down with nitrogen to remove the bulk of the reaction mixture prior to introduction of the regeneration solution. The fouled TS-1 catalyst was regenerated in situ with a regeneration solution of water, $H_2O_2$ and methanol. The operating temperature was 80° C. The regeneration process was done batch-wise with the regeneration solution having a methanol concentration of between 11 and 15 wt %. The initial concentration of $H_2O_2$ in the regeneration solution, i.e., the concentration of $H_2O_2$ in the regeneration solution prior to contact with the fouled TS-1 catalyst, was 1.401 wt %. When the $H_2O_2$ regeneration solution depleted to about 0.1 wt %, a pre-calculated amount of 35 wt % $H_2O_2$ solution was injected into the depleted regeneration solution to bring the concentration back to about 1 wt %; see Table VIII for initial batch concentrations and following concentrations of solution after each injection. After the regeneration process, the reactants were fed back at the same conditions as the initial epoxidation reaction in this Example.

TABLE VIII

| Batch | $H_2O_2$ concentration Wt % | Methanol concentration Wt % |
|---|---|---|
| 1 | 1.4 | 14 |
| 2 | 1.0 | 12.9 |
| 3 | 0.8 | 11.4 |
| 4 | 0.3 | 11.3 |
| 5 | 0.15 | 11.6 |

Table IX shows the epi productivity, epi selectivity and $H_2O_2$ concentration in the effluent at four different time periods using a fresh TS-1 catalyst, in particular, after one hour of operation the first sample was analyzed. After 4 hours of operation, when the Epi productivity reached a maximum amount, the second sample was analyzed. After 12 hours of operation the third sample, an intermediate datum, was analyzed. After 17 hours of operation, when a steady state was reached, the fourth sample was analyzed.

TABLE IX

Fresh TS-1 Catalyst

| Hours of operation | Epi Production lbs/hr/ft³ cat | Epi selectivity % | $H_2O_2$ concentration in effluent Wt % |
|---|---|---|---|
| 1 | 9.0 | 85.7 | 0.6 |
| 4 | 12.7 | 70.7 | 3.9 |
| 12 | 11.5 | 83.4 | 8.8 |
| 17 | 9.2 | 82.9 | 11.8 |

Table X shows the epi productivity, epi selectivity and $H_2O_2$ concentration in the effluent at three different time periods using the regenerated catalyst: in particular, after one hour of operation the first sample was analyzed. After 4 hours of operation, when the epi productivity reached a maximum amount, the second sample was analyzed. After 12 hours of operation, immediately prior to termination of the epoxidation reaction, the third sample was analyzed.

TABLE X

Regenerated TS-1 Catalyst

| Hours of operation | Epi Production lbs/hr/ft³ cat | Epi selectivity % | $H_2O_2$ concentration in effluent Wt % |
|---|---|---|---|
| 1 | 3.5 | 86.3 | 0.4 |
| 4 | 12.9 | 86.5 | 3.9 |
| 12 | 10 | 85.5 | 12.0 |

In comparing Tables IX and X, one can see that regenerating a titanium silicate catalyst with a solution containing $H_2O_2$/water/MeOH improved the selectivity by 2.1%, comparing the 12$^{th}$ hour of operation.

Figure 2:
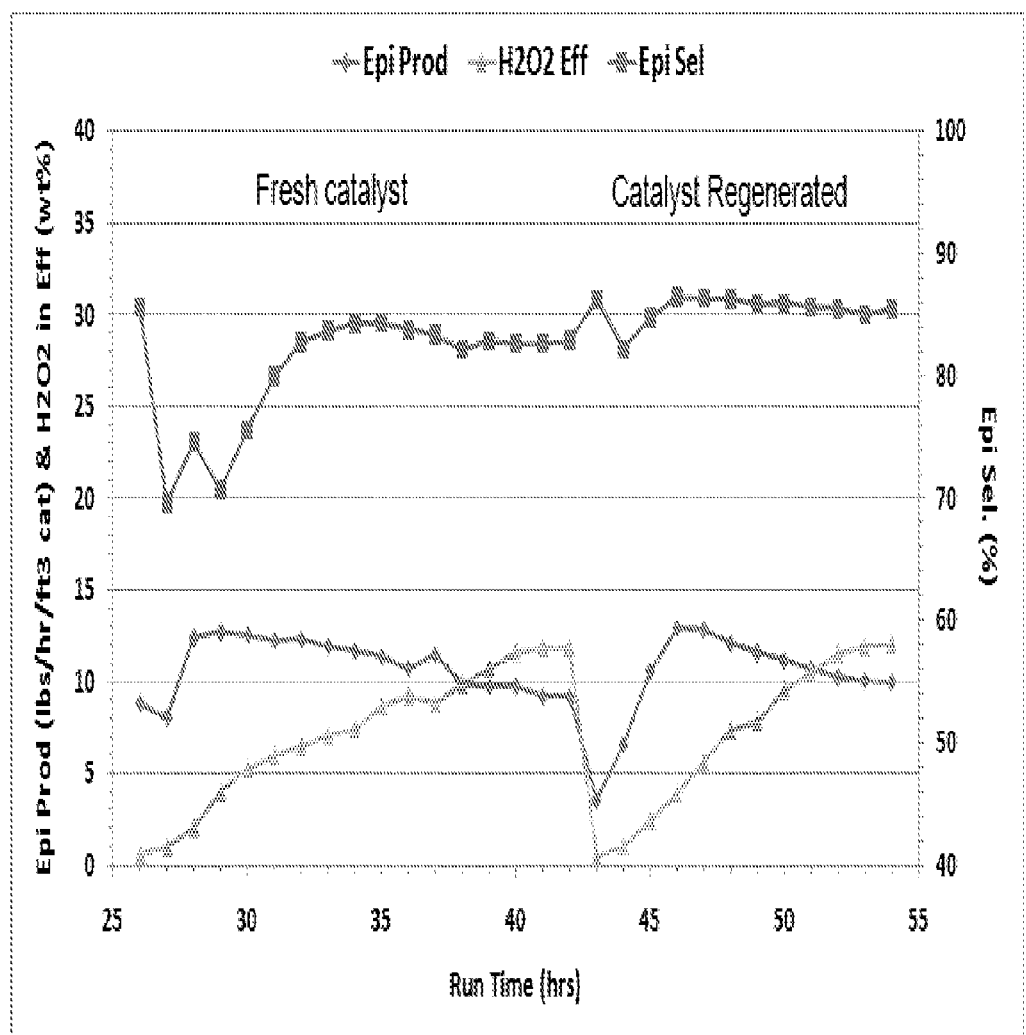
FIG. 2 is a graph depicting epi productivity, epi selectivity and $H_2O_2$ concentration data generated by a process according to certain embodiments of the present disclosure.

Turning now to FIG. 2, the epi productivity, epi selectivity and $H_2O_2$ concentration in the effluent using the fresh catalyst and the catalyst regenerated with the regeneration solution of water, $H_2O_2$ and methanol are graphically depicted. FIG. 2 shows plotted data generated from Example 5, represented as follows: epi productivity by diamonds; $H_2O_2$ concentration in effluent by triangles; and epi selectivity by squares. It can be seen that selectivity improved and that the productivity and $H_2O_2$ concentration follow similar patterns as before.

Examples 6-9 and Comparative Example C

The fresh catalyst used for Examples 6-9 and Comparative Example C was the same type of fresh TS-1 catalyst used in Examples 1-3, above (see Table 1 for epi yield data). For the purposes of Examples 6-9 and Comparative Example C, a fouled TS-1 catalyst is in particular a catalyst that delivers an epi yield less than that of a fresh catalyst under same or similar conditions, e.g., 96% of the yield delivered by a fresh catalyst. For the purposes of Examples 6-9, a regenerated TS-1 catalyst is a TS-1 catalyst that has been regenerated and then partially dried in a vacuum oven at 60° C. for 15 minutes and contains 30 wt % of other components, based on a total weight of the regenerated TS-1 catalyst. Results of Examples 6-9 and Comparative Example C are provided in Table XI.

Example 6

A fouled TS-1 catalyst (10.1 g, equivalent to 7.8 g fresh TS-1) was added to a 750 mL jacketed glass reactor with a stainless steel cooling coil, thermocouple, mechanical stirrer, addition funnel, $N_2$ purge with gas scrubber, and reflux condenser/cold finger combination. A regeneration solution (350.3 g) having an oxidizing agent concentration of 2.0 wt % hydrogen peroxide, 35.0% methanol and 63% de-ionized water was added to the reactor to form a mixture. The mixture was stirred at 600 revolutions per minute (rpm) and maintained at approximately 40° C. using the cooling coil. After 60 minutes the mixture was drained from the reactor into two 250 mL centrifuge tubes, and then centrifuged at 10000 rpm at 0° C. for 10 minutes.

The regeneration solution was decanted from the regenerated TS-1 catalyst and the amount of peroxide remaining in the regeneration solution was determined by iodometric titration with sodium thiosulfate to be 1.96%. The regenerated TS-1 catalyst was recovered by decantation and dried in a vacuum oven at 60° C. for 15 minutes.

Example 7

A fouled TS-1 catalyst (10.0 g, equivalent to 7.8 g fresh TS-1) was added to a 750-mL jacketed glass reactor with a stainless steel cooling coil, thermocouple, mechanical stirrer, addition funnel, $N_2$ purge with gas scrubber, and reflux condenser/cold finger combination. A regeneration solution (352.2 g) having an oxidizing agent concentration of 0.5 wt % hydrogen peroxide, 20.0% methanol and 79.5% de-ionized water was added to the reactor to form a mixture. The mixture was stirred at 600 revolutions per minute (rpm) and maintained at approximately 40° C. using the cooling coil. After 60 minutes the mixture was drained from the reactor into two 250 mL centrifuge tubes, and then centrifuged at 10000 rpm at 0° C. for 10 minutes.

The regeneration solution was decanted from the regenerated TS-1 catalyst and the amount of peroxide remaining in the regeneration solution was determined by iodometric titration with sodium thiosulfate to be 0.17%. The regenerated TS-1 catalyst was recovered by decantation and dried in a vacuum oven at 60° C. for 15 minutes.

Example 8

A fouled TS-1 catalyst (10.1 g, equivalent to 7.8 g fresh TS-1) was added to a 750-mL jacketed glass reactor with a stainless steel cooling coil, thermocouple, mechanical stirrer, addition funnel, $N_2$ purge with gas scrubber, and reflux condenser/cold finger combination. A regeneration solution (349.7 g) having an oxidizing agent concentration of 5 wt % hydrogen peroxide, 5% methanol and 90% de-ionized water was added to the reactor to form a mixture. The mixture was stirred at 600 revolutions per minute (rpm) and maintained at approximately 40° C. using the cooling coil. After 60 minutes the mixture was drained from the reactor into two 250 mL centrifuge tubes, and then centrifuged at 10000 rpm at 0° C. for 10 minutes. The regeneration solution was decanted from the regenerated TS-1 catalyst and the amount of peroxide remaining in the regeneration solution was determined by iodometric titration with sodium thiosulfate to be 4.0%. The regenerated TS-1 catalyst was recovered by decantation and dried in a vacuum oven at 60° C. for 15 minutes.

Example 9

A fouled TS-1 catalyst (10.0 g, equivalent to 7.8 g fresh TS-1) was added to a 750-mL jacketed glass reactor with a stainless steel cooling coil, thermocouple, mechanical stirrer, addition funnel, $N_2$ purge with gas scrubber, and reflux condenser/cold finger combination. A regeneration solution (350.0 g) having an oxidizing agent concentration of 1.0 wt % hydrogen peroxide, 95.0% methanol and 4.0% de-ionized water was added to the reactor to form a mixture. The mixture was stirred at 600 revolutions per minute (rpm) and maintained at approximately 40° C. using the cooling coil. After 60 minutes the mixture was drained from the reactor into two 250 mL centrifuge tubes, and then centrifuged at 10000 rpm at 0° C. for 10 minutes. The regeneration solution was decanted from the regenerated TS-1 catalyst and the amount of peroxide remaining in the regeneration solution was determined by iodometric titration with sodium thiosulfate to be 0.82%. The regenerated TS-1 catalyst was recovered by decantation and dried in a vacuum oven at 60° C. for 15 minutes.

Comparative Example C

The same fouled catalyst as used in Examples 6-9 was used, but it was not subjected to a regeneration process.
Epoxidation Reaction Using the Regenerated Catalysts from Example 6-9

Allyl chloride (52.0 wt %), methanol (5.2 wt %), 1,2-dichlorobenzene (23.0 wt %), and the regenerated TS-1 catalyst from each of Examples 6-9 (2.00 wt %, equivalent to 1.55 wt % fresh catalyst) were added to a 750-mL jacketed glass reactor with a stainless steel cooling coil, thermocouple, mechanical stirrer, addition funnel, $N_2$ purge with gas scrubber, and reflux condenser/cold finger combination. The contents of the reactor were brought to 25.5° C. After the reactor contents were brought to 25.5° C., a peroxide compound (30 wt %/aq. hydrogen peroxide, 17.8 wt % total solution, 5.3 wt % $H_2O_2$) was added to the addition funnel to form a reaction mixture. The reaction mixture was stirred at 600 rpm, and the reaction mixture was maintained at approximately 40° C. using the cooling coil. After 60 minutes the reactor mixture was drained equally into two 250 mL centrifuge tubes, and then centrifuged at 10000 rpm and 0° C. for 10 minutes.

The liquid was decanted from the regenerated TS-1 catalyst into a reparatory funnel and allowed to separate into a liquid organic phase and a liquid aqueous phase. The liquid organic phase and the liquid aqueous phase were analyzed by GC.

TABLE XI

| Example | Epi Yield |
|---|---|
| 6 | 89.6% |
| 7 | 88.9% |
| 8 | 88.6% |
| 9 | 89.5% |
| Comparative Example C | 86.3% |

What is claimed is:

1. A process for regenerating a titanium silicalite catalyst fouled during a reaction between an olefin and a peroxide compound to produce an oxirane, the process comprising contacting the fouled titanium silicalite catalyst with a regeneration solution including at least one oxidizing agent to provide a regenerated titanium silicalite catalyst, wherein the regeneration solution has a pH of less than 2 and an oxidizing agent concentration of less than 0.50 weight percent based on a total weight of the regeneration solution prior to contact with the fouled titanium silicalite catalyst, exclusive of the titanium silicalite catalyst.

2. The process of claim 1, further including adjusting the pH of the regeneration solution to less than 2 prior to contacting the fouled titanium silicalite catalyst with the regeneration solution.

3. The process of claim 1, further including washing the regenerated titanium silicalite catalyst with an organic compound.

4. The process of claim 1, wherein the regeneration solution has an oxidizing agent concentration in a range of from 0.10 weight percent to 0.49 weight percent, based on the total weight of the regeneration solution, exclusive of the titanium silicalite catalyst.

5. A process for regenerating a titanium silicalite catalyst fouled during a reaction between an olefin and a peroxide compound to produce an oxirane, the process comprising the step of contacting the fouled titanium silicalite catalyst with a regeneration solution having a pH of less than 2 and comprising at least one oxidizing agent and further comprising an organic compound to provide the regenerated titanium silicalite catalyst, with the proviso that the process does not comprise a washing step in addition to the contacting step.

6. The process of claim 5, wherein the at least one oxidizing agent concentration is in a range of from 0.1 wt % to 50 wt % based on the total weight of the regeneration solution prior to contact with the fouled titanium silicalite catalyst, exclusive of the titanium silicalite catalyst.

7. The process of claim 5, wherein the regeneration solution comprises the organic compound in a range of from 1 to 95 weight percent based on the total weight of the regeneration solution.

8. The process of claim 5, wherein the organic compound is an aliphatic, cyclic, aromatic, halogenated, supercritical, or alcoholic organic diluent.

9. The process of claim 8, wherein the organic compound comprises methanol.

10. The process of claim 5, wherein the regeneration solution further comprises an effluent from the reaction between the olefin and the peroxide compound.

11. The process of claim 5, wherein the at least one oxidizing agent is selected from the group hydrogen peroxide, ozone, organic peroxide compounds, inorganic peroxide compounds, and combinations thereof.

12. The process of claim 5, wherein the peroxide compound is hydrogen peroxide, wherein the oxirane is epichlorohydrin and wherein the olefin is allyl chloride.

13. A regenerated titanium silicalite catalyst obtainable by the process as claimed in claim 1.

14. The process of claim 3, wherein the organic compound is an aliphatic, cyclic, aromatic, halogenated, supercritical, or alcoholic organic diluent.

15. The process of claim 13, wherein the organic compound comprises methanol.

16. The process of claim 1, wherein the regeneration solution further comprises an effluent from the reaction between the olefin and the peroxide compound.

17. The process of claim 1, wherein regenerating the titanium silicalite catalyst is carried out at a temperature in the range of 0 degrees Celsius to 100 degrees Celsius.

18. The process of claim 1, wherein the at least one oxidizing agent is selected from the group hydrogen peroxide, ozone, organic peroxide compounds, inorganic peroxide compounds, and combinations thereof.

19. The process of claim 1, wherein the peroxide compound is hydrogen peroxide, wherein the oxirane is epichlorohydrin and wherein the olefin is allyl chloride.

* * * * *